US00PP20166P3

(12) United States Plant Patent
Carruth

(10) Patent No.: US PP20,166 P3
(45) Date of Patent: Jul. 7, 2009

(54) FLORIBUNDA ROSE PLANT NAMED 'WEKJUTONO'

(50) Latin Name: *Rosa hybrida*
Varietal Denomination: WEKjutono

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 65 days.

(21) Appl. No.: 11/985,120

(22) Filed: Nov. 14, 2007

(51) Int. Cl.
*A01H 5/00* (2006.01)

(52) U.S. Cl. ..... Plt./146

(58) Field of Classification Search ..... Plt./146
See application file for complete search history.

(56) References Cited

U.S. PATENT DOCUMENTS

PP9,161 P 6/1995 Harkness
PP17,175 P2 10/2006 Carruth

*Primary Examiner*—Susan B McCormick Ewoldt
(74) *Attorney, Agent, or Firm*—McKee, Voorhees & Sease, P.L.C.

(57) ABSTRACT

A new variety of Floribunda rose suitable for garden decoration, having flowers of bright orange coloration.

1 Drawing Sheet

Classification: The present invention relates to a new *Rosa hybrida* plant.

Variety denomination: The new plant has the varietal denomination 'WEKjutono'.

BACKGROUND OF THE INVENTION

This invention relates to a new and distinct variety of Floribunda Rose. It has as its seed parent the variety known as 'WEKlezpat' (U.S. Plant Pat. No. 17,175) and as its pollen parent the variety known as 'MACamster' (not patented).

SUMMARY OF THE INVENTION

Among the features which distinguish the new variety from other presently available and commercial rose cultivars known to the inventor are the following combination of characteristics: its many stipitate glands on the surface of the bud, its red suffusion on the inner surface of the sepal that appears as the flower ages, its unique bright orange flowers coloration and its dark mahogany red suffusion on the young leaves. The plant has a rounded moderately spreading growing habit, suitable for outdoor garden decoration.

Asexual reproduction of the new variety by budding as performed in Kern County and Pomona, Calif. shows that the foregoing and other distinguishing characteristics come true to form and are established and transmitted through succeeding asexual propagations. 'WEKjutono' may be asexually propagated by budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKlezpat' by the following combination of characteristics: whereas 'WEKjutono' bears double flowers (about 27 to 44 petals) of bright orange coloration, 'WEKlezpat' bears very double flowers with significantly heavier petalage (about 48 to 72 petals) of butter gold blushed pink coloration. The new variety is classified as a floribunda rose with a rounded moderately spreading medium height growing habit (about 82 to about 96 cm. in height), whereas the seed parent is classified as a hybrid tea rose with an upright moderately spreading significantly taller growing habit (about 152 to about 170 cm. in height).

The new variety may be distinguished from its pollen parent 'MACamster' by the following combination of characteristics: whereas 'WEKjutono' bears flowers of bright orange coloration, 'MACamster' bears flowers of glowing gold coloration. The new variety has a rounded moderately spreading medium height growing habit (about 82 to about 96 cm. in height), whereas the pollen parent has an upright significantly taller growing habit (about 90 to about 120 cm. in height).

COMPARISON WITH THE CLOSEST COMMERCIALLY AVAILABLE CULTIVAR

The new variety may be distinguished from its closest commercially available cultivar, 'HARwelcome' (U.S. Plant Pat. No. 9,161) by the following combination of characteristics: whereas 'WEKjutono' bears double flowers (about 27 to 44 petals) of bright orange coloration, 'HARwelcome' bears double flowers with significantly lesser petalage (about 25 to 30 petals) of blended orange coloration. The new variety has a rounded moderately spreading medium height growing habit (about 82 to about 96 cm. in height), whereas the closest commercially available cultivar has a bushy upright medium height significantly taller growing habit (about 105 to 130 cm in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

Botanical designation:

The new variety botanical designation is *Rosa hybrida* 'WEKjutono'.

Flower:

The new variety usually bears its flowers singly. Flowers are borne on strong short stems (about 13 to about 31 cm.). Outdoors, the plant blooms abundantly and nearly continuously during the growing season. The flowers have a moderate tea to somewhat spicy fragrance.

Bud:

The peduncle is about 1.8 to about 3.9 cm. in length, of somewhat heavy caliper (about 0.3 to about 0.4 cm. in diameter), and usually erect. It is moderately smooth, with some stipitate glands and few hairs. Peduncle color is between 146B and 146A sometimes lightly suffused, especially on the side exposed to the sun, with between 187B and 187A.

Before the calyx breaks, the bud is about 1.3 to about 1.9 cm. in diameter at the widest point, about 1.6 to about 2.3 cm. in length, and moderately pointed to somewhat ovoid in shape with a conspicuous neck. The surface of the bud bears few small foliaceous appendages and many stipitate glands, sometimes with slender entire foliaceous parts extending beyond the tip of the bud about ¼ or more of its length. Bud color is between 137C and 137B often lightly suffused, especially on the side exposed to the sun, with between 187B and 187A.

The sepals are about 2.2 to about 3.4 cm. in length and about 0.9 to about 1.2 cm. in width at the widest point. The outer surface color of the sepal is between 137C and 137B often lightly suffused, especially on the side exposed to the sun, with between 187B and 187A. The inner surface color of the sepal is between 139A and 137A. After the sepals open, the inner surface color is often heavily suffused, especially on the area exposed to the sun, with between 187A and 187B. The sepals are covered with fine wooly tomentum; sepal margins are lined with many stipitate glands and some hairs.

The receptacle of the flower is of medium length (about 1.1 to about 1.5 cm.) and somewhat heavy in caliper (about 1.2 to about 1.6 cm. in diameter). The receptacle is somewhat cup-shaped, flat at the top and rounded at its base. Its surface is very smooth sometimes with few hairs and with thick fleshy walls. The receptacle color is between 144A and 146A.

As the petals open (after the calyx breaks), the bud is about 1.8 to about 2.2 cm. in diameter at the widest point, about 2.5 to about 3.2 cm. in length, and ovoid in form. The color of the under surfaces of the newly opened petals is between 31A and 26A often moderately blushed with between 34A and 35A. At the point where the petal attaches, there is a somewhat large zone of between 3B and 2B. The color of the upper surfaces of the newly opened petals is between 30C and 30B. At the point where the petal attaches, there is a moderately large zone of between 9A and 12A.

Bloom:

When fully open, the bloom ranges from about 8.7 to about 11.8 cm. in diameter. Petalage is double with about 27 to 44 petals and about 3 to 11 petaloids irregularly arranged. When partially open, the bloom form is moderately cupped to somewhat high centered, and the petals are loosely spiraled to cupped with petal edges somewhat reflexed outward. When fully open, the bloom form is more cupped, and the petals are cupped with petal edges moderately reflexed outward.

Petals:

The substance of the petals is somewhat heavy and of thin thickness, with upper surfaces moderately satiny and under surfaces almost matte to slightly shiny. The petals are about 2.3 to about 5.4 cm. in length and about 1.8 to about 4.8 cm. in width at the widest point. Petal margins are entire.

The outer petals are moderately obovate in shape with rounded apices. The inner petals are moderately obovate to somewhat oblanceolate in shape with rounded apices.

Petaloids are about 1.2 to about 2.8 cm. in length and about 0.7 to about 1.6 cm. in width at the widest point. Petaloids are irregularly shaped moderately oblanceolate to somewhat subulate with rounded apices.

Newly opened flower:

The under surface color of the outer petals is between 21D and 19A sometimes lightly blushed with between 28A and 30A. At the point where the petal attaches, there is a somewhat large zone of between 13B and 12B. The upper surface color of the outer petals is between 22B and 24B often moderately blushed with between 28A and 35A. At the point where the petal attaches, there is a moderately large zone of between 13A and 14B.

The under surface color of the intermediate and inner petals is between 24B and 23C sometimes lightly blushed with between 28A and 30A. The upper surface color of the intermediate and inner petals is between 24A and 24B often moderately blushed with between 28A and 35A.

The under and upper surface color of the petaloids are similar in coloration to the upper and under surfaces of the intermediate and inner petals.

The general tonality of the newly opened flower is between 24A and 24B often moderately blushed with between 28A and 35A.

Three-day-old flower:

The under surface color of the outer, intermediate and inner petals is between 19A and 22B sometimes lightly blushed with between 51A and 47C. At the point where the petal attaches, there is a somewhat large zone of between 13B and 12B. The upper surface color of the outer, intermediate and inner petals is between 21B and 23C often moderately blushed with between 46A and 47C. At the point where the petal attaches, there is a moderately large zone of between 13B and 12A.

The under and upper surface color of the petaloids are similar in coloration to the upper and under surfaces of the intermediate and inner petals.

The general tonality of the three-day-old flower is between 21B and 23C often moderately blushed with between 46A and 47C.

On the spent bloom, the petals usually drop off cleanly.

In October in Pomona, Calif. blooms on the bush growing outdoors generally last about four to five days. Cut roses from plants grown outdoors and kept at normal indoor living temperatures generally last about four to five days.

Male reproductive organs:

Stamens are many in number (average about 155) and are arranged regularly about the pistils; a few are mixed with petaloids. The filaments are of somewhat short length (about 0.6 to about 1.1 cm.) most with anthers. Filaments are between 14B and 13B in color. The anthers are moderately small for the class and all open approximately at the same time. Anther color when immature is near 23B on the external part and near 11B on the internal part. Anther color at maturity is near 165B on the external part and near 200A on the internal part. Pollen is abundant and between 16C and 15D in color.

Female reproductive organs:

Pistils vary in number (average about 110). The styles are moderately even, somewhat long in length (about 0.6 to about 0.9 cm.), thin in caliper, and loosely bunched to somewhat separated. Stigma color is between 8A and 9C. Style color is between 2C and 150C sometimes lightly suffused near the top with near 53B. Ovaries are usually all enclosed in the calyx.

Hips are of average length (about 1.2 to about 1.5 cm.), rounded in form, and between 25A and 28A in color when ripe. The hip surface is very smooth with thick fleshy walls. The sepals are moderately permanent and usually straight in shape.

The seeds are irregularly rounded, smooth in texture, approximately 23 to about 31 per hip, about 0.4 to about 0.7 cm. in diameter at the widest point and between 163C and 164C in color.

Foliage:

The compound leaves are usually comprised of three to five leaflets and are borne abundantly. The five-leaflet leaves are about 7.8 to about 12.1 cm. in length and about 5.7 to about 8.7 cm. in width at the widest point, moderately heavy to somewhat crisp in texture, and moderately glossy in finish. The terminal leaflets are about 3.7 to about 6.8 cm. in length and about 2.7 to about 4.1 cm. in width at the widest point, shaped moderately ovate to somewhat oval with acute to somewhat acuminate apices and rounded to slightly acute bases. Their margins are usually simply serrate.

The upper surface color of the mature leaf is between 147A and 137A. The under surface color of the mature leaf is between 147B and 148A. The upper surface color of the young leaf is between 147A and 137A, usually heavily suffused with between 187A and 183A. The under surface color of the young leaf is between 139C and 138B, usually heavily suffused with between 187B and 183A.

The rachis is average in caliper and moderately rough. The upper side is deeply grooved with few hairs and some stipitate glands on the edges of the grooves. The under side of the rachis is moderately rough with some stipitate glands and few small prickles. The rachis color is near 145A on the under side and near 137C on the upper side.

The stipules are about 0.9 to about 1.5 cm. in length and of somewhat wide width (about 0.4 to about 0.7 cm.) with medium length straight points that usually turn out at an angle of more than 45 degrees and sometimes recurve toward the stem. The stipules color is between 137C and 146D.

The petiole is average in caliper and moderately rough. The upper side is deeply grooved with few hairs and some stipitate glands on the edges of the grooves. The under side of the petiole is moderately rough with some stipitate glands and few small prickles. The petiole is about 0.7 to about 1.5 cm. in length and about 0.1 to about 0.15 cm in diameter at the widest point. The petiole color is near 145A on the under side and near 137C on the upper side.

The plant displays an average degree of resistance to powdery mildew and rust as compared to other commercial varieties grown under comparable conditions in Pomona, Calif. The plant's winter hardiness and drought/heat tolerance are yet to be determined.

Growth:

The plant has a rounded moderately spreading medium height growing habit (about 82 to about 96 cm. in height and about 60 to about 82 cm. spread at the widest point), with full branching. It displays moderately vigorous growth and the canes are of somewhat heavy caliper for the class.

The color of the major stems is between 146A and 147B. They bear many large prickles that are about 0.6 to about 1.0 cm. in length. The large prickles are angled slightly downward with a very long narrow oval base; prickle color is between 165B and 166C. The major stem bears some small prickles of similar shape and coloration.

The color of the branches is between 146A and 148A. They bear many large prickles which are of similar size and shape to the large prickles on the major stems; prickle color is between 160B and 160A sometimes lightly suffused with near 53D. The branches bear some small prickles of similar shape and coloration.

The color of the new shoots is between 146C and 137A often heavily suffused with between 187B and 187A. They bear many large prickles which are of similar size and shape to the large prickles on the major stems; prickle color is between 152B and 152C usually moderately suffused with between 187C and 187D. The shoots bear some small prickles of similar shape and coloration.

I claim:

1. A new and distinct Floribunda rose plant of the variety substantially as described and illustrated herein.

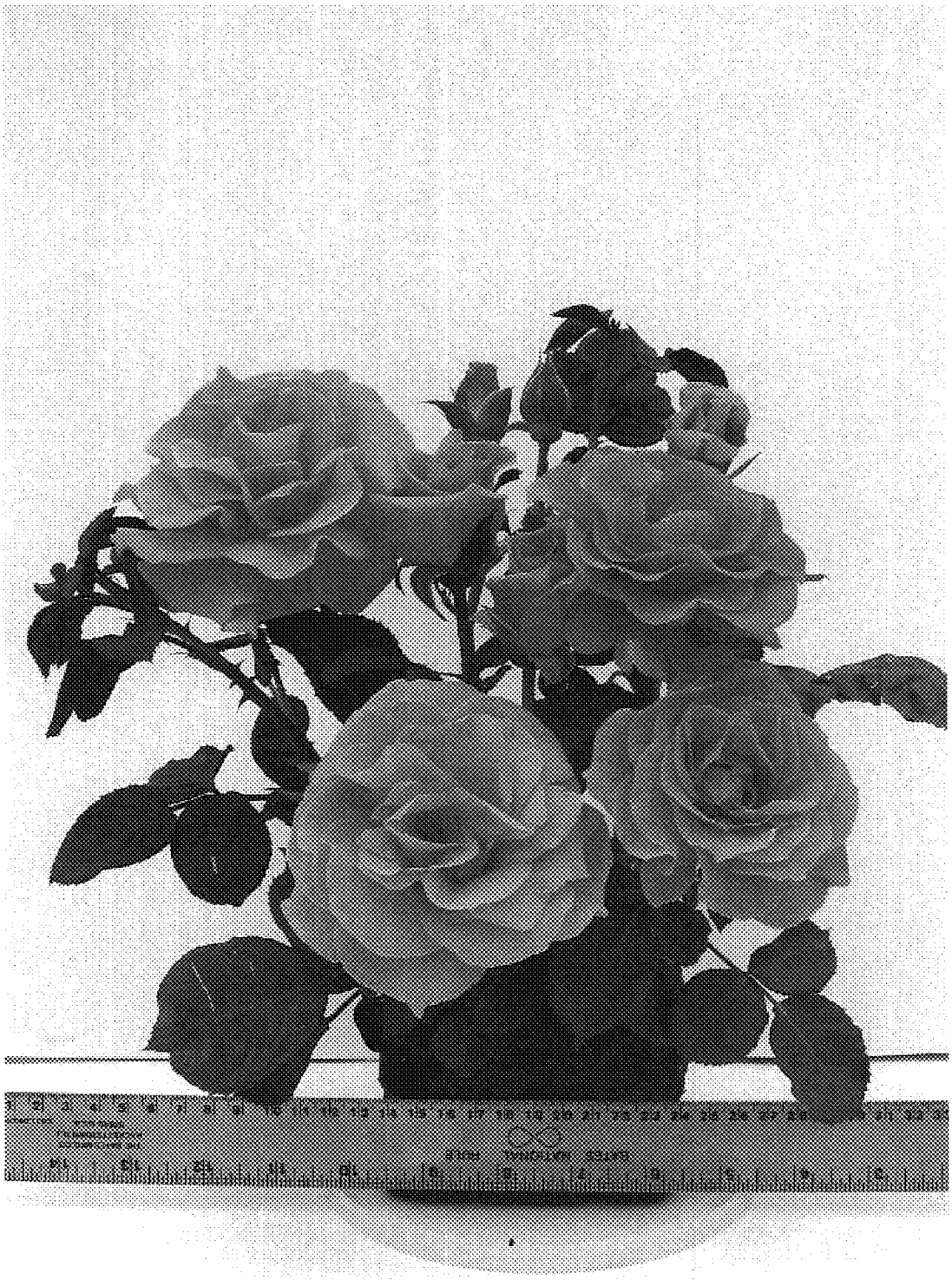

* * * * *